(12) United States Patent
Kramer et al.

(10) Patent No.: US 8,109,891 B2
(45) Date of Patent: Feb. 7, 2012

(54) DEVICE AND METHOD FOR DETECTING AN EPILEPTIC EVENT

(75) Inventors: Uri Kramer, Ramat Hasharon (IL);
Amos Shaham, Even-Yehuda (IL); Shai Shpitalnik, Yehud (IL); Noam Weissman, Bnei-Braq (IL); Yael Goren, Ramat Gan (IL); Uri Kartoun, Ramat-Hasharon (IL)

(73) Assignee: Biolert Ltd, Ramat Hasharon (IL)

( * ) Notice: Subject to any disclaimer, the term of this patent is extended or adjusted under 35 U.S.C. 154(b) by 0 days.

(21) Appl. No.: 12/067,174

(22) PCT Filed: Sep. 19, 2006

(86) PCT No.: PCT/IL2006/001093
§ 371 (c)(1),
(2), (4) Date: Mar. 17, 2008

(87) PCT Pub. No.: WO2007/034476
PCT Pub. Date: Mar. 29, 2007

(65) Prior Publication Data
US 2009/0137921 A1    May 28, 2009

(51) Int. Cl.
*A61B 5/117* (2006.01)
*A61B 5/103* (2006.01)

(52) U.S. Cl. ...................................... 600/595

(58) Field of Classification Search .................. 600/300, 600/587, 595, 534, 529, 586; 340/573.4, 340/566, 693, 573.7, 573.1, 573.6; 200/61.45 R; 702/190, 14, 15, 17, 18; 128/903, 905; 285/12, 285/13; 356/28.5, 477
See application file for complete search history.

(56) References Cited

U.S. PATENT DOCUMENTS

| | | | |
|---|---|---|---|
| 5,523,742 A * | 6/1996 | Simkins et al. | 340/573.7 |
| 5,610,590 A * | 3/1997 | Johnson et al. | 340/573.4 |
| 6,570,503 B1 * | 5/2003 | Ulert et al. | 340/573.1 |
| 7,269,537 B1 * | 9/2007 | Mattern | 702/190 |
| 7,314,451 B2 * | 1/2008 | Halperin et al. | 600/534 |
| 2006/0064037 A1 * | 3/2006 | Shalon et al. | 600/586 |

* cited by examiner

*Primary Examiner* — Brian Szmal
(74) *Attorney, Agent, or Firm* — Naomi Assia Law Offices

(57) ABSTRACT

The invention discloses an epileptic event alert system, capable of detecting and analyzing whether motions sensed by at least one motion sensor of the system, are related to an epileptic seizure event. The system may be utilized for detection of additional motion-related pathologies. A detection method is similarly disclosed, as is computer-readable media adapted to perform the detection method of the invention.

27 Claims, 21 Drawing Sheets

General Epilepsy Movement / Daily Movement distinctions

| Signal Parameter | Epilepsy Seizures Movement | Normal Daily Movement |
|---|---|---|
| Duration | Long (minutes to hours) | Various |
| Frequency (typical) | Tonic- Hi: 5 -15Hz<br>Clonic (impulse) - Lo: 0.5-3Hz | Very Low to Hi |
| Frequency variation | Random changes | Mostly Stable |
| Amplitude | Random changes | Mostly Stable |
| Direction of Movement | Random changes (detected by the 3D accelerometer) | Mostly Stable |
| Association: Amp. / Hi Freq (Tonic). | Hi Freq is associated with Low to Medium Amplitude | Hi Freq is associated with Very low Amp. |

Fig. 3

| Parameter | Freq | Freq. Variations Short Term | Freq. Variations Long Term | Amp | Amp Variations | Direction Variation | Event Duration |
|---|---|---|---|---|---|---|---|
| Epilepsy Movements | | | | | | | |
| Tonic Low Amp | MID TO HI | LO | MID | LO | LO | LO | LONG |
| Clonic Fast | MID | MID | HI | MID | MID | MID | MID |
| Clonic Slow | LO | MID | HI | HI | MID | HI | MID |
| Tonic/Clonic | ALTERNATES | HI | V. HI | ALTERNATES | ALTERNATES | HI | LONG |
| Daily Movements | | | | | | | |
| Walking | LO | LO | LO | MID | LO | LO | LONG |
| Typing | MID | HI | V. HI | V. LO | MID | MID | MID |
| Exercising /Running | MID | LO | LO | HI | LO | LO | LONG |
| Tennis | V. LO | HI | HI | MID-HI | HI | HI | LONG |
| Gardening - Shearing | V.LO - LO | HI | HI | HI | MID | MID | ANY |
| Talking w/ Hands | LO | HI | HI | LO | MID | HI | SHORT |
| Scratching head | LO | LO | LO | LO | LO | LO | SHORT |
| Stretching (hands) | HI | LO | LO | LO | LO | HI | SHORT |

Fig. 4

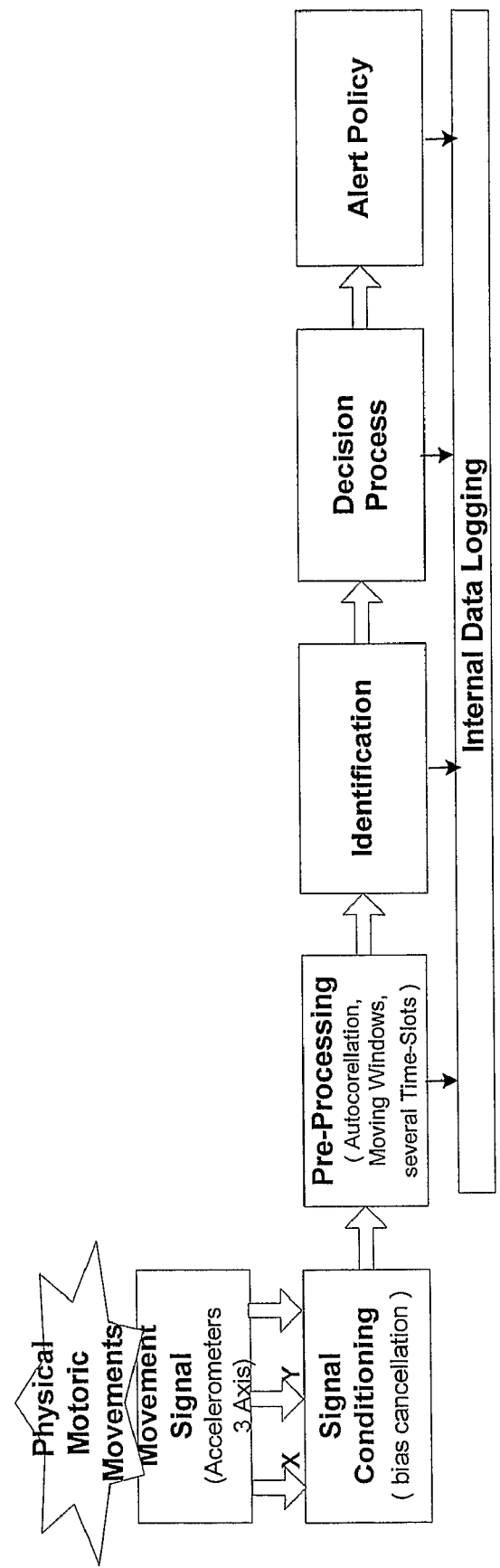
Fig. 5 - Functional Blocks of Motion Signal Proceesing

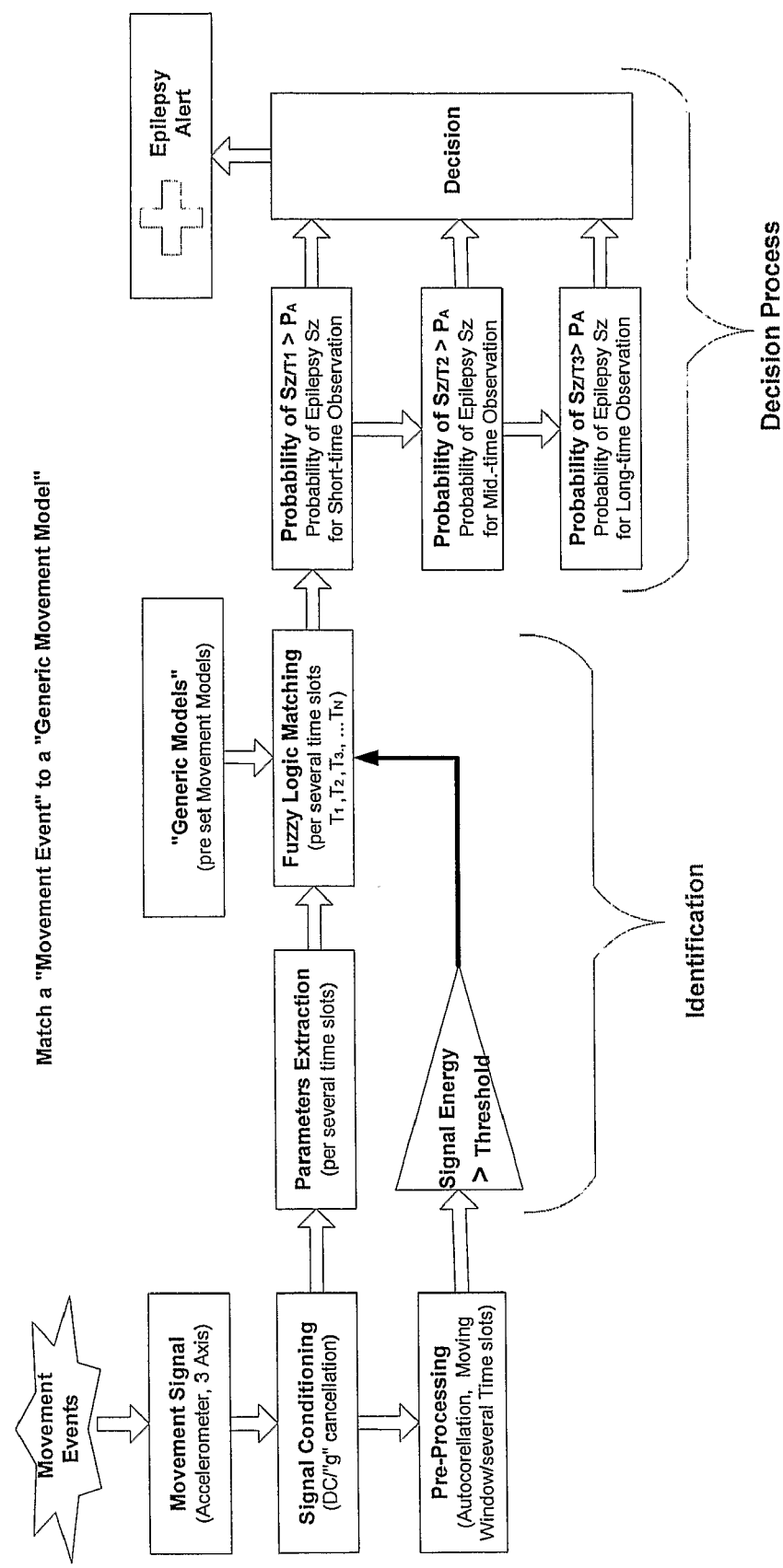

DEVICE AND METHOD FOR DETECTING AN EPILEPTIC EVENT

FIELD OF THE INVENTION

The present invention relates generally to the field of monitoring devices. More specifically, the present invention relates to a system and method for detecting epileptic events in a user.

BACKGROUND

Epilepsy, a neurological disorder characterized by the occurrence of seizures (specifically episodic impairment or loss of consciousness, abnormal motor phenomena, psychic or sensory disturbances, or the perturbation of the autonomic nervous system), is debilitating to a great number of people. The prevalence of epilepsy is 0.7% of the population with as many as two million Americans that suffer from various forms of epilepsy and around 50 million worldwide. Research has found that its prevalence may be even greater worldwide, particularly in less economically developed nations, suggesting that the worldwide figure for epilepsy sufferers may be in excess of one hundred million.

A typical epilepsy patient experiences episodic attacks or seizures, which are generally defined as periods of abnormal neurological activity. The characteristics of an epileptic seizure onset are different from patient to patient, but are frequently consistent from seizure to seizure within a single patient. Because epilepsy is characterized by seizures, its sufferers are frequently limited in the kinds of activities they may participate in. Epilepsy can prevent people from driving, working, or otherwise participating in much of what society has to offer. Some epilepsy sufferers have serious seizures so frequently that they are effectively incapacitated. Furthermore, epilepsy is often progressive and can be associated with degenerative disorders and conditions. Over time, epileptic seizures often become more frequent and more serious, and may lead to deterioration of other brain functions (including cognitive function) as well as physical impairments.

Timely detection of seizures allows a caregiver to monitor their severity and duration and to determine whether immediate treatment is necessary. Attempts have been made to create alarm systems based on motion systems, which alert a caregiver or call for emergency services in response to a repetitive rhythmic movement, which could indicate a seizure. One example is described in U.S. Pat. No. 6,361,508. However, these systems suffer from an abundance of false alarms, since rhythmic movement is also associated with many types of everyday activity, such as walking, hand gesturing, and even typing. Most known systems are placed under the mattress of a patient, and are unsuitable for wear during an active day. An example is described in U.S. Pat. No. 4,320,766.

Nijsen et al. compared the efficiency of accelerometers to detect seizures to that found using EEG and video readings (Nijsen et al., Epilepsy & Behavior 7, (2005), 74-84), and stated that accelerometers do not require patients to be stationary as does EEG equipment, which is most readily available in hospitals. Nijsen performed visual analysis of the plotted signals (as presented on a chart recorder) but did not perform any numerical or statistical analysis on the accelerometer readings which would allow an accelerometer to be used as a stand-alone detection method. Use of an accelerometer alone, without statistical analysis, would result in a high degree of false positives due to rhythmic movement present in many everyday activities. As stated in Nijsen, "Visual analysis of ACM [accelerometer] readings is very labor intensive . . . it is more difficult to find suitable parameters that make computerized detection possible". Nijsen therefore recognized the need to develop a computerized system which would serve as an alert system allowing normal ambulation.

Other systems, such as WO 03/001996, necessitate implanted electrodes, and rely on EEG readings obtained from the brain. Another type of system is described in WO 02/082999A1, which describes computerized analysis of video images taken of the patient in order to determine whether movement shown in a series of images is similar to that of an epileptic seizure.

The need exists for an improved method, and system for detecting an epileptic event in an epilepsy sufferer. The system should not interfere with everyday activities, and should allow freedom of movement. Such an improved system should have a low rate of false positive alerts, yet should successfully detect epileptic seizures when they occur.

SUMMARY OF THE INVENTION

An epileptic event alert system comprising:
A detection and analysis unit comprising:
a) one or more motion sensors adapted to produce an electrical signal corresponding with mechanical movement of the detection and analysis unit;
b) a microcontroller comprising
  i. non-volatile memory adapted to store at least one set of motion signal parameters associated with epileptic motion and at least another set of parameters associated with non-epileptic motion;
  ii. computer readable software and dedicated hardware adapted to compare at least one signal parameter of the signal produced by said one or more sensors against at least one of said stored sets of motion signal parameters;
c) a communication unit adapted to transmit an alert signal to a remote location;
d) a control circuit adapted to interact with said communication unit, and adapted to activate said computer readable software (ii) upon the signal meeting a threshold level.

According to one embodiment, each motion sensor produces a separate signal, and the separate signal produced by each given sensor includes information relating to motion of the detection and analysis unit in a direction corresponding with an orientation of the given sensor. In such case, any one or more of the separate signals reaching the threshold level causes the control circuit to activate said the software for signal processing. The control circuit induces a power-saving mode in said system when the signal has not reached the threshold level for a predefined duration time.

Moreover, in certain embodiments, the signal produced by said one or more sensors is an analog signal and said signal processing unit further comprises an analog to digital converter.

In the preferred embodiment, the signal processing software is adapted to output a seizure probability value based on a comparison of parameters of the signal produced by said one or more sensors and the stored set of motion signal parameters associated with epileptic motion. The seizure probability value is additionally based on a comparison of parameters of the signal produced by said one or more sensors and the stored set of motion signal parameters associated with non-epileptic motion. The seizure probability value is positively related to a correlation between the sensor signal parameter with one or more parameters in the parameter set associated with epileptic movement. The seizure probability value is inversely related to a correlation between the sensor signal parameter with one or more parameters in the parameter set associate with non-epileptic movement.

In the preferred embodiment, the system further comprises an alert decision unit adapted to produce a local alert signal based on the seizure probability value, and based on a predefined duration of signal. In such case, the local alert signal produced by said decision unit is adapted to trigger said communication unit to transmit a remote alert signal. Preferably, the system further comprises a switch operable by the user, for deactivating a local alert signal prior to a remote alert signal being triggered.

Additionally, in certain embodiments, the communication unit includes a communication circuit selected from the group consisting of a Bluetooth circuit, WiFi circuit, a ZigBee, and a GPRS circuit.

Moreover, the system may further comprise an output signal for instructing an epileptic treatment unit to administer an epileptic treatment in response to an alert signal. The epileptic treatment unit may apply a treatment substantially automatically in response to either a local or remote alert signal, or may be adapted to be triggered by a treatment signal initiated remotely and received through said communication unit.

Preferably, the controller is adapted to initiate a self-test.

Additionally, the system may further comprise a microphone for detecting sounds originating by the user and from the vicinity of a user, and said communication unit is adapted to transmit said sounds detected by said microphone.

Preferably, said control circuit is adapted to trigger a "no motion alert" when no motion signals are detected during a predefined period of time.

Preferably, the signal parameters produced by said motion sensor and said stored epileptic motion signal parameters, are selected from at least one of the following group:
the frequency of the motion, frequency variation over time, the amplitude of the signal, amplitude variations over time, the relative direction of the motion, the direction variation over time, and the duration of the motion.

In certain embodiments, the system is adapted to be worn upon the limb of a user. The system may have the general appearance of a wristwatch.

The present invention additionally provides a method of detecting an epileptic seizure comprising:
a) fastening at least one motion sensors to the limb of a user, said sensor adapted to produce an electrical signal corresponding with mechanical movement of the sensor;
b) measuring said electrical signal produced by said at least one motion sensor and performing computerized processing of said signal to obtain signal motion parameters;
c) comparing said signal parameters of said measured electrical signal, against at least one stored set of epileptic motion signal parameters and/or against at least one set of non-epileptic epileptic motion signal parameters; wherein said comparison is performed using computerized processing means;
d) outputting a seizure probability value based on said comparison;
e) transmitting an alert signal to a remote location, using a communication unit, if said seizure probability value is within a predetermined range of values.

In the method, preferably, the signal parameters measured by said motion sensor and said stored epileptic motion signal parameters, are comprised of at least one of the following: the frequency of the motion, frequency variation over time, the amplitude of the signal, amplitude variations over time, the relative direction of the motion and direction variations, and the duration of the motion.

In certain embodiments, the method further comprises a step of autocorrelation, performed during said step (b). Said autocorrelation may be performed upon a single measured by each sensor, and/or may be performed upon signals measured by different sensors within the system.

In other embodiments, the method further comprises a step of removal of DC bias, performed during said step (b).

The invention additionally provides computer-readable media adapted to perform steps (b), (c) and (d) of the method.

In certain embodiments, the computer-readable media is further adapted to control and initiate transmission of an alert signal to a remote location, using a communication unit, if said seizure probability value is within a predetermined range of values.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 3 illustrates a Table of parameters associated with typical epileptic seizure motions, as compared with the parameters of normal daily movement.

FIG. 4 illustrates additional signal parameters measured by a motion sensor, for specific types of epileptic seizures, as compared to the signal parameters measured for different types of normal daily activities.

FIG. 5 shows a block diagram illustrating functional blocks of signal processing according to some embodiments of the present invention;

FIG. 6 shows a flow diagram including the step of a method of signal processing which may be performed according to some embodiments of the present invention;

Figure 1:
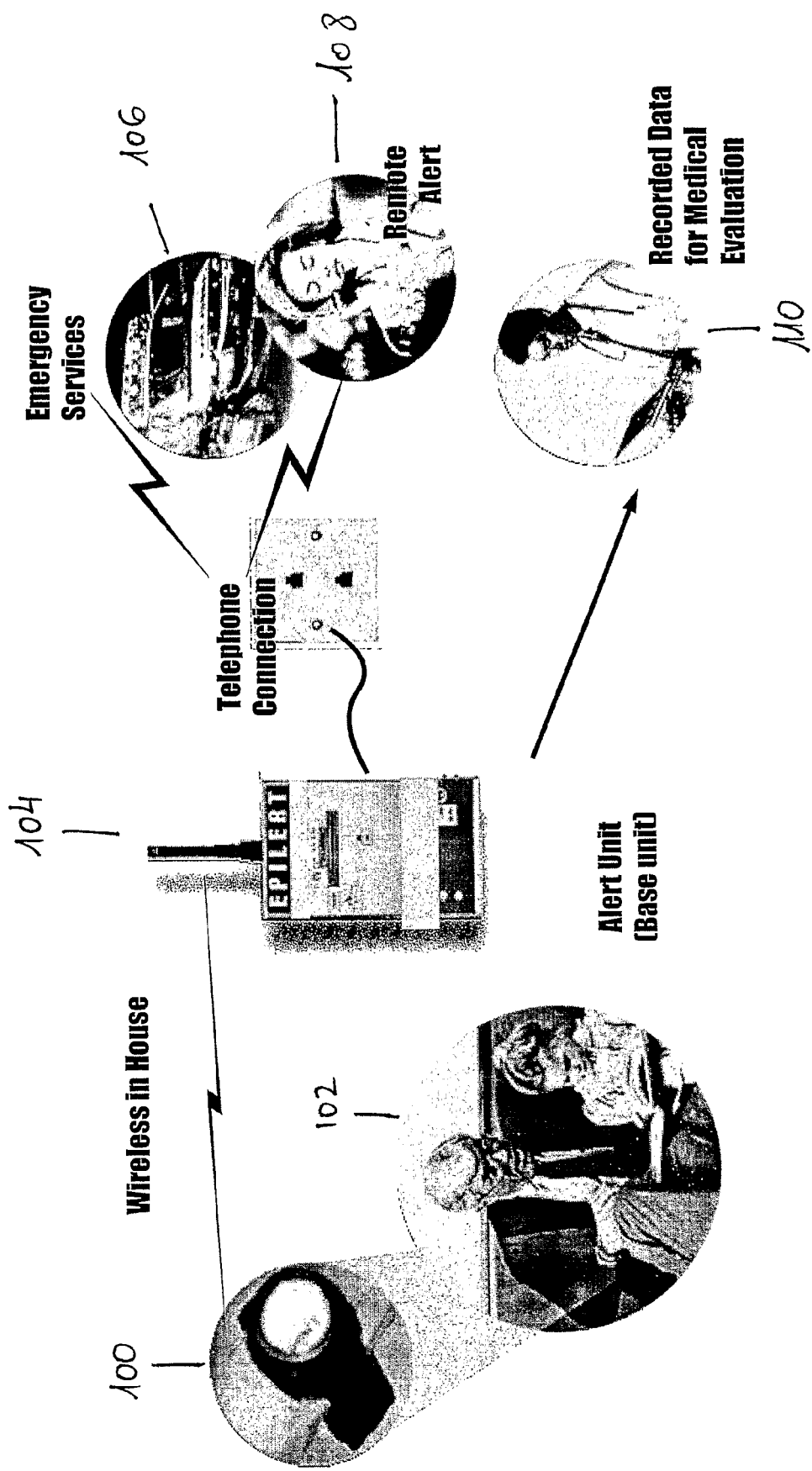
FIG. 1 shows an overview of the system according to the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, components and circuits have not been described in detail so as not to obscure the present invention.

Unless specifically stated otherwise, it is appreciated that throughout the specification, the terms "processing", "computing", "calculating", "determining", or the like, refer to the action and/or processes of a computer or computing system, or similar electronic computing device. Such action manipulates and/or transforms data represented as physical, such as electronic, quantities within the computing system's registers and/or memories into other data similarly represented as physical quantities within the computing system's memories, registers or other such information storage, transmission or display devices.

The present invention provides an epileptic event alert system, which is a capable of measuring the extent and relative direction of motion an individual is currently undergoing. The system is capable of analyzing whether the motion is similar to that occurring in a seizure and dissimilar to that seen in a plurality of everyday activities which an individual may undertake. The system utilizes computerized processing to evaluate the motion characteristics, and to output a seizure probability value. If the value is within a predetermined range, the system causes an alert signal to be transmitted to a remote location via a communication unit. The alert signal may be transmitted to the individual's family, to medical personnel or to emergency services.

Optionally, the system may transmit a local alert signal which the individual can switch off in case of a false alarm, before the alert is transmitted to a remote location. A predefined time is allowed to pass before the remote alert is sent, to allow the user sufficient time to deactivate a false alarm.

Referring to FIG. 1, an overview of the system is shown. The central component of the system is termed the "detection and analysis unit" 100, and may have the form of a wristwatch, which the patient 102 wears upon a limb (arm or leg). Preferably, the individual is aware from previous seizures which limb tends to undergo the most movement during a seizure (the "predominant seizure limb"), and attaches the detection and analysis unit 100 to this limb. The detection and analysis unit 100 preferably contains a 3D accelerometer, generally termed a "motion sensor", capable of producing an appropriate electrical signal corresponding with mechanical movement of the sensor in any given direction. Alternatively, a 2D or 1D accelerometer may be used. The extent of the motion is measured and analyzed using several parameters, discussed hereinbelow. The processing unit present within the detection and analysis unit 100 utilizes the software of the invention to compare these parameters to at least one set of parameters associated with an epileptic seizure, and/or to at least one set of parameters associated with normal activity. A seizure probability value is reached and outputted. Optionally, the value may be outputted to a display as well. If the value is within a predetermined range, an alert signal is sent in a wireless manner via a communication unit to a local alert unit 104 present in the patient's house. The alert unit 104 communicates with the communication unit, which in turn, utilizes a telephone to reach emergency services 106, or the patient's family 108.

Figure 2A:
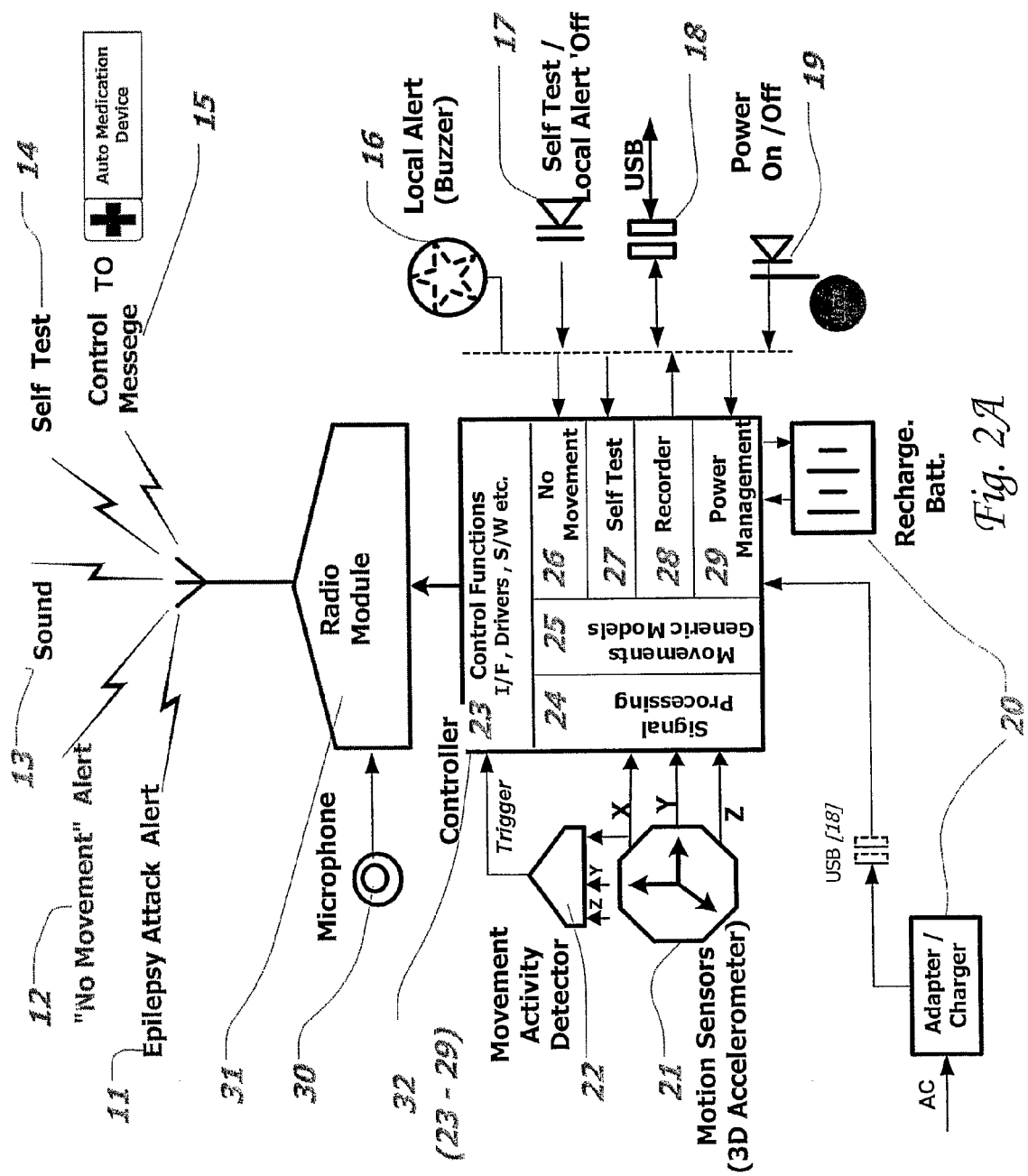
FIG. 2A is a block diagram of the system, depicting sensors, a microphone, a control circuit, a signal processing unit running the software of the invention, non-volatile memory and a communication unit.

Referring to FIG. 2A, the components of the detection and analysis unit are shown in a block diagram.

A movement activity detector 22 is shown, connected to a 3D accelerometer, also known more generally as a motion sensor 21. The movement activity detector 22 will detect movements and will activate the central components of the detection analysis unit only when the motion signal measured by the accelerometer passes a minimal threshold. This results in power saving, since minimal components of the system are active during periods of low motion.

Preferably, the accelerometer is a MEMS (micro-electromechanical device) such as ADXL330 produced by Analog Devices, USA.

The motion sensor 21 outputs a separate electrical signal for movement in each of the X, Y, Z axes. The X Y Z analog outputs are fed to three 'Analog to Digital' converters. The analog to digital conversion process may take place within a general processor or within the motion sensor.

A microcontroller 32 is in communication with all other components of the system, and is configured to oversee the control functions 23 such as the maintenance and operation software, drivers, interfaces, etc. When the signal is sent from the motion sensors 21, and is sensed by the movement activity system 22 to be over a certain threshold, the signal processing unit 24 is triggered to activate the software of the invention and begin signal analysis. The parameters of the movement are compared to sets of parameters stored in non-volatile memory. The stored parameters are associated with either known epileptic seizures, or are associated with non-epileptic movements. Sets of stored parameters are illustrated in the Figure as "movement generic models" 25. Signal processing will be performed by the software using associated hardware, so that after the comparison is performed, a seizure probability is outputted and a decision is reached by the microcontroller 32 whether to activate a local alert 16 or an epilepsy attack alert 11, which is transmitted via the radio module 31 to an alert unit (shown in FIG. 1).

The alert unit includes communication means to transmit the alert via telephone or cellular telephone networks, to a remote location at which medical personnel or family members are present.

The radio module 31 acts as a transmitter/receiver. In a preferred embodiment, an RF Activity LED is present on the detection and analysis unit and will indicate when the communication link with the alert unit is operative. A breakage in this link will cause a specific alarm to be sounded.

Optionally, a microphone 30 is present in the detection and analysis unit, and is activated when an alert is activated, to transmit sounds produced by the user to a remote location. The sounds may be indicative of a seizure.

Optionally, a self-test 17 may be performed in which an end-to-end assessment of the system ascertains that the system and the radio link between the detection and analysis unit, and the alert unit, is active. The self-test additionally checks most of the circuits in these units. The test is initiated by the user. When initiated, a 'Self-test Radio Message' [14] is sent to the alert units (not shown). The alert units will perform a local S.T. procedure and will respond back to the detection and analysis unit. If this response reaches the detection and analysis unit, LED lights or a buzz will be turned on to indicate that the overall system is OK.

Optionally, a USB connection 18 is provided to allow data to be transferred from the detection and analysis unit to a computer or to magnetic media. Additionally, software can be loaded and system settings can be inputted via the USB connection.

An on/off switch 19 is included.

In order to ascertain that the user is indeed wearing the detection unit at all times, the system outputs a "no movement" signal 12 when no movement is measured by the motion sensors 21 over a predetermined amount of time. A "no movement alert" 12 is signaled audibly in such case at the alert unit.

Rechargeable batteries 20 are used, which may be attached to an adaptor for recharging.

Power management 29 circuitry sends the signal processing 24 software and other elements into power-saving mode when the signal has not reached the threshold level for a predefined duration time. This results in saving and is advantageous over prior-art systems, since it allows long-life of the battery before the need to recharge or change the battery. A relatively small battery may now be used, and the detection and analysis unit can be wearable and not uncomfortable or overly large.

A recorder 28 may be included in the detection and analysis unit, allowing the processed and analyzed data to be saved and retrieved in future by medical personnel.

The system may operate to cover an area equal to that found in a typical house. The alert unit includes communication means, which sends the signal to a more remote location, such as to a hospital, off-site relatives, etc.

The communication unit may include a communication circuit selected from: a Bluetooth circuit, WiFi circuit, a ZigBee, and a GPRS circuit or standard radio devices.

In certain embodiments, the system may activate a cellular telephone, or may contain circuitry having cellular-like and GPS qualities capable of contacting a cellular network for transmitting the alert and patient location to a remote location. This would allow the detection and analysis unit to be worn and be operative in various locations other than the user's own home.

Optionally, in addition to outputting an alert signal, the system may output a signal to an epileptic treatment unit in the patient's vicinity, instructing the treatment unit to administer an epileptic treatment. Such a treatment may constitute for example, administration of an injected drug, or administration of an electric shock.

Certain parameters of the signal produced by the motion sensor, undergo analysis and computerized comparison to stored parameters of known epileptic motion, and comparison to non-epileptic motion. This allows determination whether the motion is a seizure or not. In the preferred embodiment, the parameters comprise the following:
the frequency of the motion, frequency variation over time, the amplitude of the signal, amplitude variations over time, the relative direction of the motion and direction variations, and the duration of the motion.

Figure 2B:
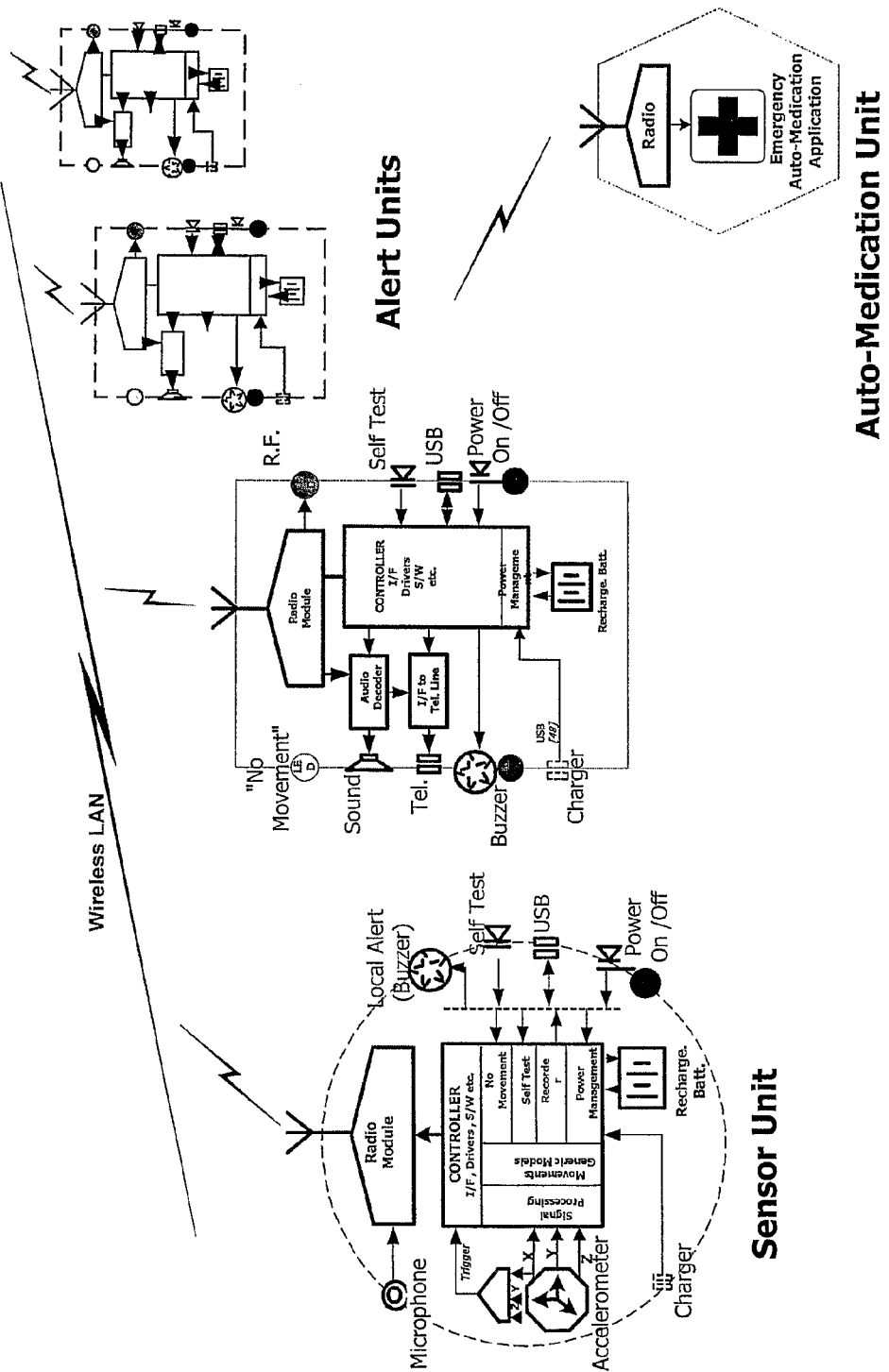
FIG. 2B illustrates the system, in which a detection and analysis unit communicating with several alert units, each having a communication unit (specifically a radio module) for communicating with the detection and analysis unit and for transmitting the alert signal to a remote location via telephone. In this embodiment, the detection and analysis unit transmits an alert to the alert units, via radio such as a local area network.

Referring to FIG. 2B, the detection and analysis unit 100 is shown, along with several alert units 102a, 102b, 102c, which contain communication units which transmit the alert signal to a remote location. In this embodiment, the detection and analysis unit 100 transmits a local alert via a local area network to the alert units 102 which are scattered within the user's house for optimal area coverage. At least one of the alert units 102(a,b,c) may be connected via a land-line or via cellular phone, to the telephone network, and communicates with medical personnel or family members upon signaling of an alert. The alert units 102(a,b,c) contain radio modules 104(a,b,c), and microcontrollers 106(a,b,c) having relevant software and hardware capabilities allowing transmission of an alert message. Included is an interface 108 with the telephone line.

Optionally, the detection and analysis unit outputs a signal to an epileptic treatment unit 110, which may administer an injected drug or an electrical shock to the patient, either in response to the alert, or in response to a signal received from remote medical personnel (via the alert unit) after they have noted transmission of the remote alert.

The system can optionally evaluate how critical the situation of the patient is (e.g. long attacks—"Status Epilepticus") and transmit a message in order to enable auto-medication.

Referring to FIG. 3, a Table is shown in which the parameters of typical epileptic seizure motions are compared with the parameters of normal daily movement. Note the duration of the movement is typically long in epileptic seizures (over 20 seconds, lasting up to minutes or hours). The repetitive pattern of movement is typically such that a 2 to 15 second window of time is typically used for analysis and identification. In comparison, movement may be brief in normal activity. Note that the direction of the movement is random in seizures, including movement repetitive in many directions. In comparison, repetitive movement stemming from normal activity will usually involve a specific direction, as may be envisioned during walking.

Referring to FIG. 4, additional signal parameters measured by a motion sensor are shown for specific types of epileptic seizures, as compared to the signal parameters measured for different types of normal daily activities. Normal activities that need to be ruled out during seizure detection, include walking, exercising, talking using hand gestures, and stretching. Parameters of the signals for these activities differ from those of epileptic seizures (e.g. clonic, tonic seizures,) as is evident from FIG. 4, and computerized analysis using the invention can successfully match the parameters to epileptic or non-epileptic motion.

Referring to FIG. 5, a flow diagram is shown indicating the central steps of the motion signal processing.

Referring to FIG. 6, a more detailed diagram is shown, allowing for instance "fuzzy logic" to be used during processing, to match the motion parameters of a user, as recorded at a given time, to one of the pre-stored sets of known parameters ("generic models"). The pre-stored sets of motion parameters represent typical epileptic motion parameters, and/or non-epileptic (healthy) motion parameters. The seizure probability value is calculated first using short windows of time, and if the value is insufficient to allow an alert/non-alert decision to be reached, the analysis will continue for longer periods of time until a decision can be reached.

Figure 7A:
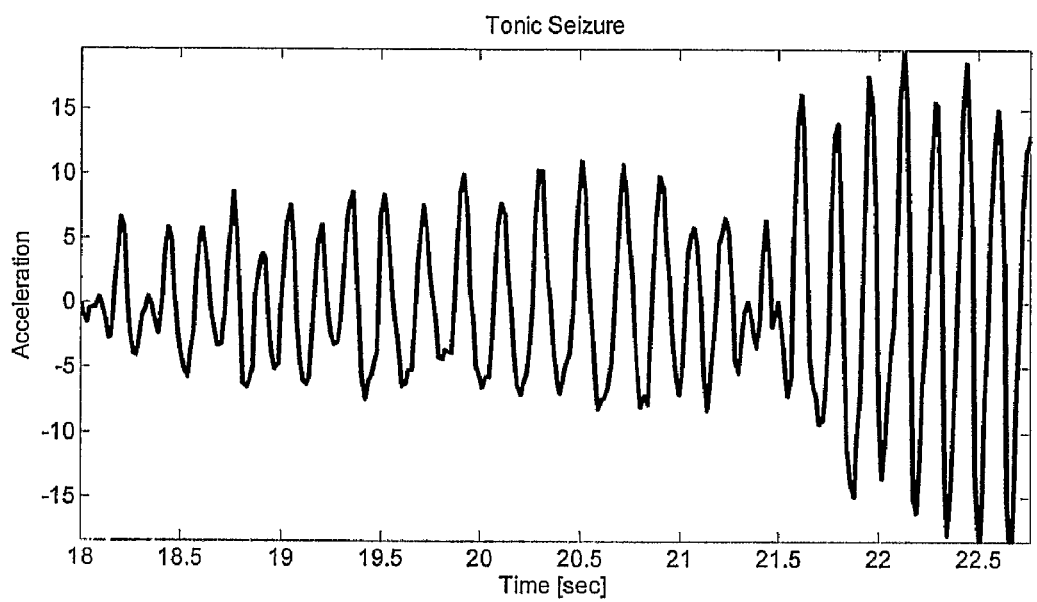
FIGS. 7A and 7B depict examples of epileptic accelerometer recordings illustrating epileptic motion signal parameters which may be processed according to some embodiments of the present invention.
Figure 7B:
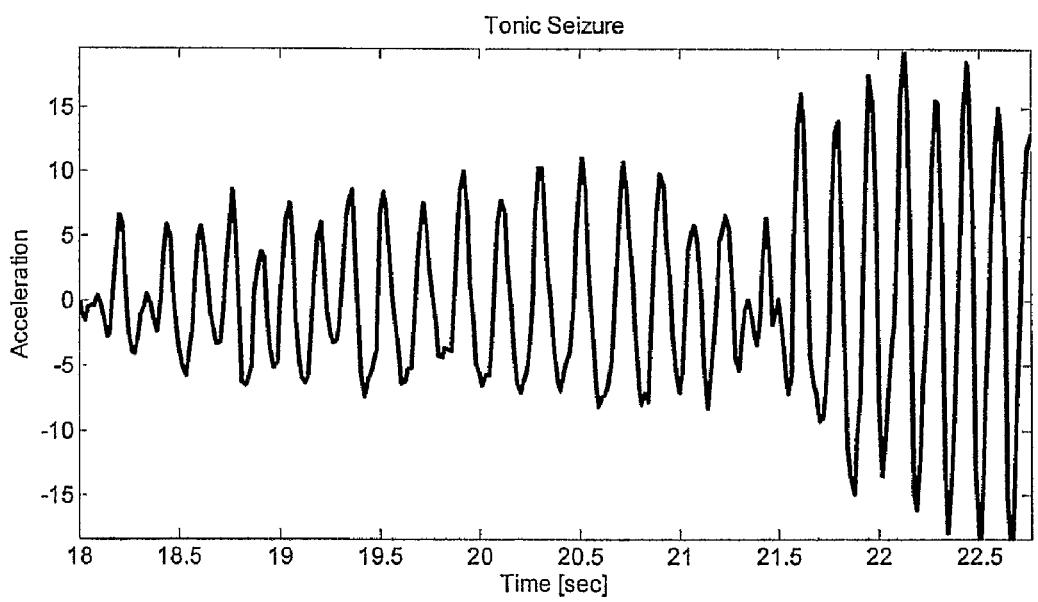

FIGS. 7A and 7B depict examples of epileptic accelerometer recordings.

In this and in other Figures, for clarity, only one channel is plotted, illustrating movement in a single axis of the X, Y, Z directional axis.

FIG. 7A demonstrates part of a clonic seizure. A clonic jolt has impulse characteristics accompanied by relaxation vibration at the tonic frequency range. This type of seizure is associated with medium frequency (slower frequency than tonic seizures, quicker frequency than regular movements). The jolt has relatively high amplitude. Its basic frequency range can be in the range of 0.5-3 Hz. For example, in the grand tonic-clonic example shown in FIG. 7A, the frequency is approximately 3 Hz, and the relative amplitude voltage is in the range of 40-80.

FIG. 7B shows a tonic seizure. It is characterized by fluctuations at high frequencies (such as 5-15 Hz) and medium amplitude (higher than regular movements). For example, in FIG. 7b, the frequency is approximately 6 Hz, and the relative amplitude voltage is approximately 5-15.

Figure 8A:
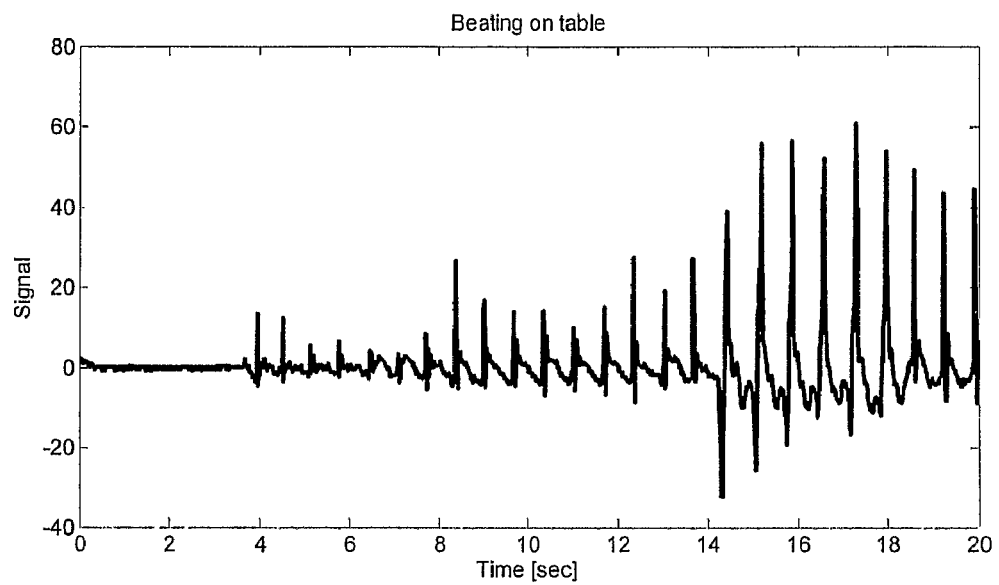
FIG. 8A shows a "Beating on the table" signal resulting from normal activity.
Figure 8B:
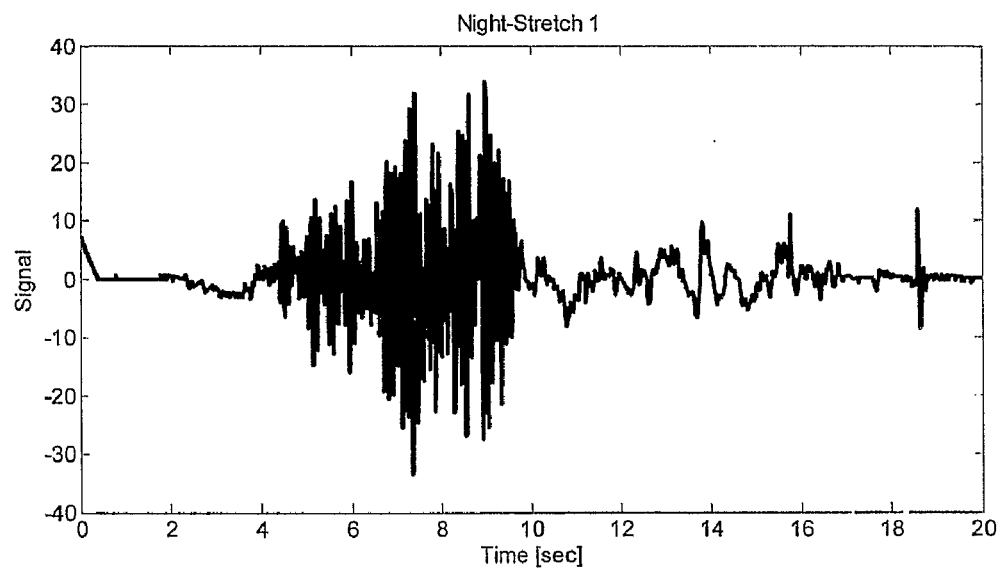
FIG. 8B illustrates normal movement occurring during a "Night-Stretch".
Figure 8C:
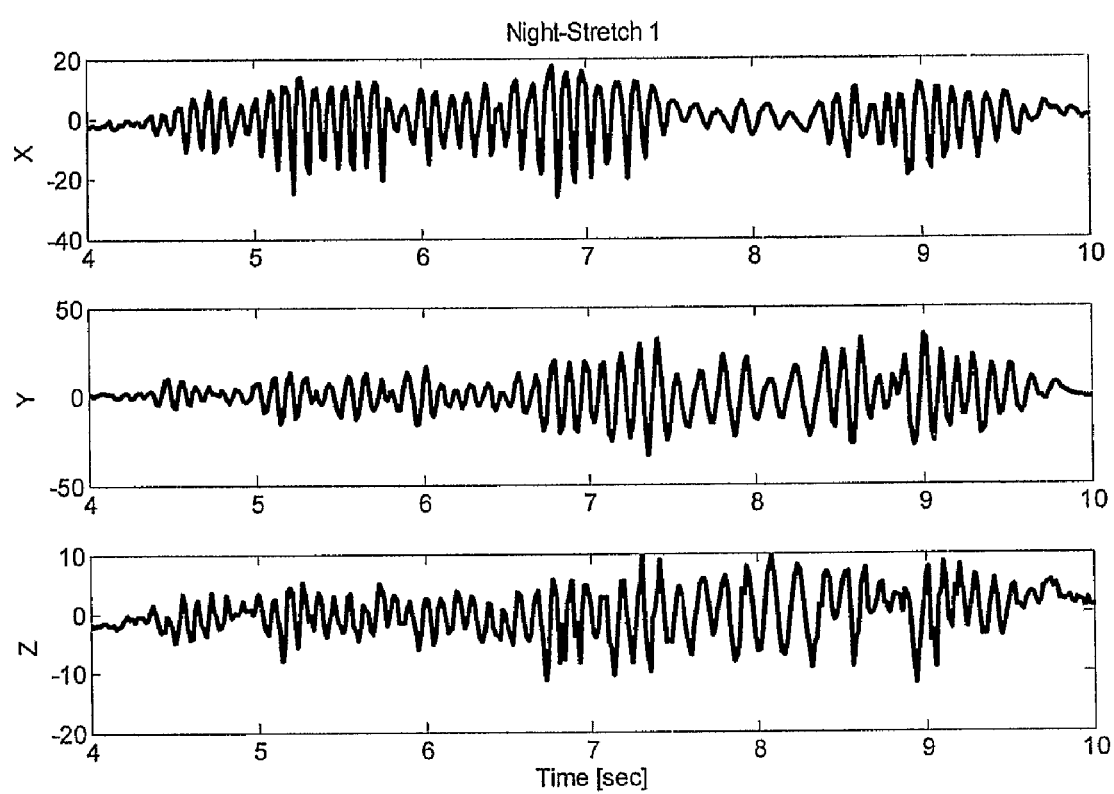
FIG. 8C shows an enlarged graph of a portion of FIG. 8B.
Figure 9:
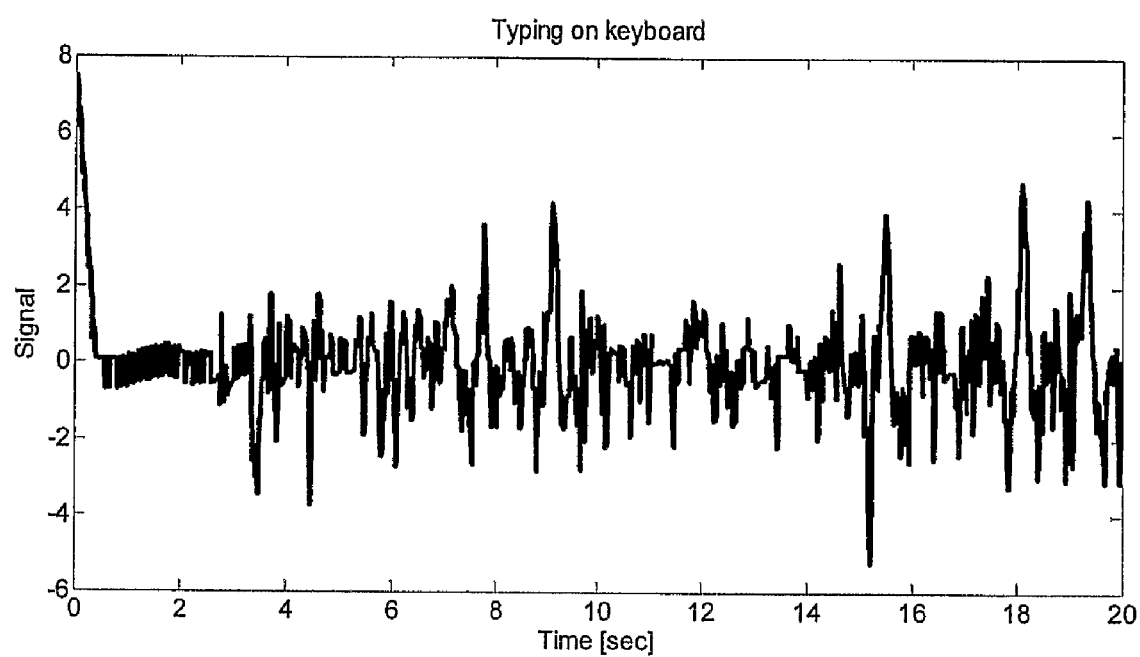
FIG. 9 illustrates a "typing on a keyboard" signal.

The graphs shown in FIGS. 8 and 9 are examples of non-epileptic acceleration recordings. For clarity, movement in only one channel (direction) is plotted.

FIG. 8A shows a "Beating on the table" signal. It is a "clonic like" movement: at medium frequency with very high amplitude.

FIG. 8B illustrates normal movement occurring during a "Night-Stretch" (stretching of the arms, as occurs during normal sleep). It is a "tonic like" motion: at high frequency and medium to low amplitude.

FIG. 8C shows zooming in on this signal. The resemblance to epileptic acceleration signal can be seen. Each graph originates in an accelerometer reading acceleration in a different axis. As in epileptic motion, this movement changes its direction with time: at the beginning, it is mainly in the X, and a bit in the Y direction, while later, the Y axis becomes the dominant direction. The movement can also be detected in the Z direction, though much weaker.

Referring to FIG. 9, a measurement obtained during typing on a keyboard results in a an extremely weak signal, as compared to an epileptic signal. The signal shown in FIG. 9 is highly random, and has little repeatability.

The analog signal outputs of the accelerometers have a DC-biased component, which is preferably corrected for. This DC bias stems from two sources—the accelerometer DC output plus the Gravitation 'g'. The DC component is preferably translated to an offset signal following autocorrelation. In a first step of the signal processing, the DC bias is calculated and deducted from the digital signal, leaving only "pure" movement signals.

To remove only the DC inherent in the sensor, a constant DC removal is enough. However, preferably. the gravitational DC influence is removed using a moving window averaging process. This time window should be short enough to follow the spatial changes of the sensor 'g', while long enough so as not to influence the spiky epileptic behavior. Thus in the preferred embodiment, a moving average (MA) is chosen as the DC removal method, changing the signals according to the equation:

new_signal=old_signal−MA(old_signal)

In the next step of signal processing for analyzing the readings of the motion sensors, an Autocorrelation process is performed on various size "time slots" using Matlab© manufactured by The MathWorks, Inc., Massachusetts, U.S.A. Autocorrelation allows periodic activity to be detected and its power/energy is calculated. If this energy is below a minimum level this "Time Slot" is rejected.

Autocorrelation is a mathematical tool for exploring the repeatability of a signal. It is the summation of the signal multiplied by itself with a short time shift. The result, as a function of this time lag, emphasizes the periods where the signals resembles itself, while diminishes the periods with opposite phases. The equation of the autocorrelation of a real signal is $$C_x(m) = \begin{cases} \sum_{n=0}^{N-m-1} x(n+m)x(n) & m \geq 0 \\ C_x(-m) & m < 0. \end{cases}$$

when x is the signal in length N.

Figure 10:
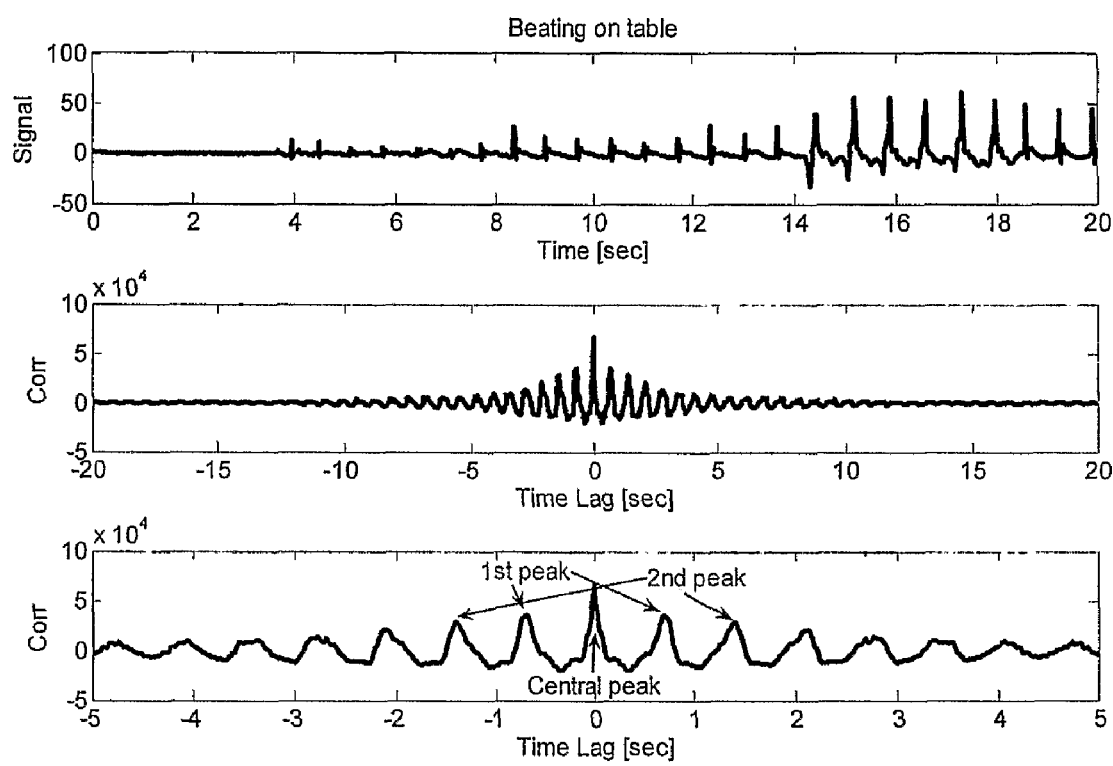
FIG. 10 illustrates a "Beating on the table" signal, and its parameters and processing are discussed.

A classic illustration of autocorrelation is that seen with a highly repetitive signal, such as measured during beating on a table, as shown in FIG. 10. The beating frequency is about 1.5 Hz, i.e. a time period of 0.67 seconds, which is also the time period between the autocorrelation peaks. The peaks are located at the signal intrinsic time period, while their values are measurements of the resemblance of the signal to itself at different times. The value of the middle peak, always at no-delay, is an indicator for the signal power. For true non-random signals, like those described herein in relation to the Figures of the invention, the autocorrelation is always symmetric around this central peak.

Autocorrelation may be performed upon a signal originating in a single axis (direction of movement), or correlation may be performed between the signals originating from several axes.

In the preferred embodiment, the relative energy level is one parameter utilized in the invention to identify the type of movement. Other preferred parameters include the Frequency, Frequency Stability/variations and Amplitude (energy) Variation between the 3 axes. These calculations are typically performed as long as the stream of signal continues, and based on periodical statistical evaluation of the parameters, a decision is made as to the type of the movement and if and when to transmit an Epilepsy Attack Alert signal.

FIGS. 10 through 19 illustrate some parameters useful for epilepsy seizure detection. The parameters and graphs are shown after DC removal has been performed from the data recorded by the accelerometers. The averaging time frame selected in the graphs is approximately 0.4 seconds.

Referring to FIG. 10, a "Beating on the table" movement was performed by a healthy individual, and the autocorrelation was plotted.

The top graph shows the digitized recorded signal of one of the channels. The central graph of FIG. 10 shows the signal's autocorrelation, and the middle portion of the signal appears in the third (lower-most) graph of FIG. 10. Three peaks are defined on the autocorrelation, which can be seen in the third graph:

The central peak is also known as the zero peak, the main peak or the zero-lag peak. As indicated by these names, the peak is located in the middle of the autocorrelation. It is always the highest peak, carrying the signal's power information. The autocorrelation is symmetrical around this peak. The autocorrelation may be normalized to its value.

The first peak—the two symmetrical peaks surrounding the central peak. Its time is the first time period of the signal's repetition. Its value, relative to the value of the main peak, yields the similarity between signal's time periods.

The second peak, which is the pair of identical peaks after the first peak, give further information about the signal's similarity to itself after a longer time lag.

The following parameters are plotted in the attached graphs:

v0—the value of the central peak
v1—the value of the first peak, relative to the main peak
t1—the time lag of the first peak
v2—the value of the second peak, relative to the main peak
t2—the time lag of the second peak
v2/v1—the value of the second peak, relative to the first peak
t2/t1—the time lag of the second peak, relative to the lag of the first peak.

In these graphs, the parameters were calculated on a 15 second autocorrelation moving window, though in the in-depth analysis other time frames, like 2 seconds, were also used. For clarity, not all the axes of the signals are plotted.

Figure 11:
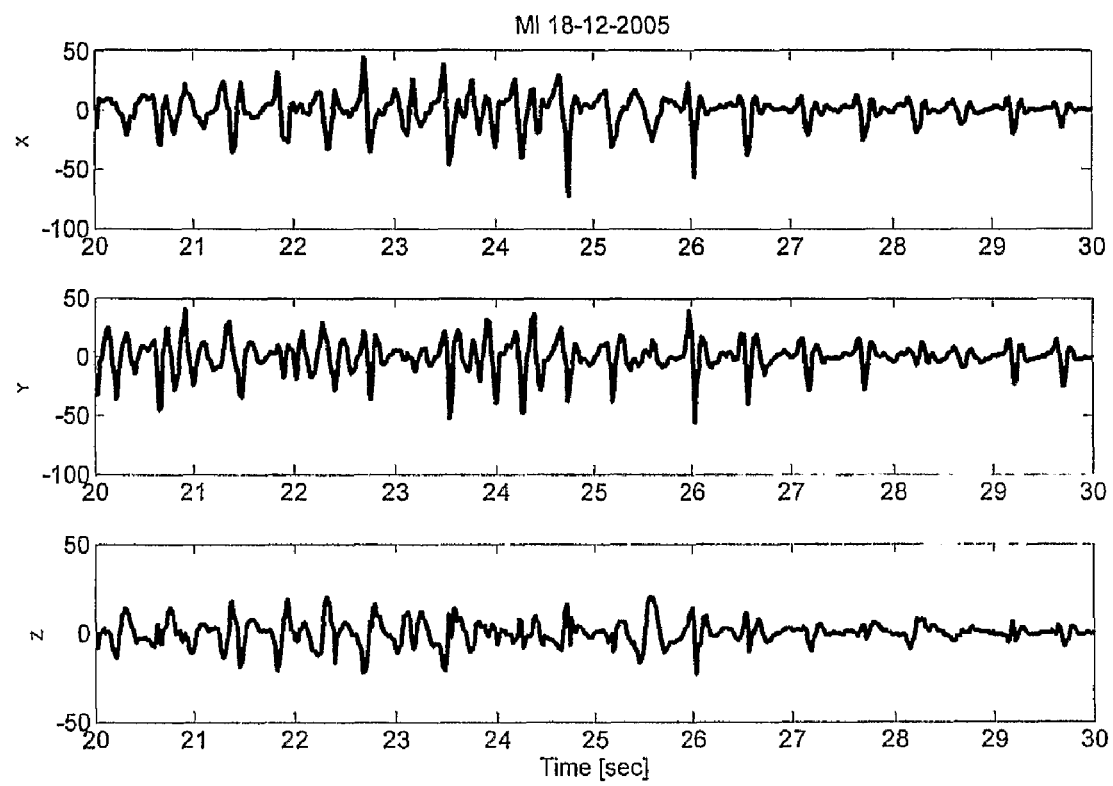
FIG. 11 is an example of 3 axial epileptic signals, after focusing on a seizure occurring during the motion sensor reading time.

FIG. 11 is an example of 3 axial epileptic signals, when zooming in on a portion of the epileptic seizure. One can observe the quick, strong fluctuations, mostly in the XY axes. Each spike resembles the previous one, but the peaks and the time between them change with time. This behavior is illustrated in the previously defined parameters, which are plotted at the following graphs, starting prior to the seizure onset.

Figure 12:
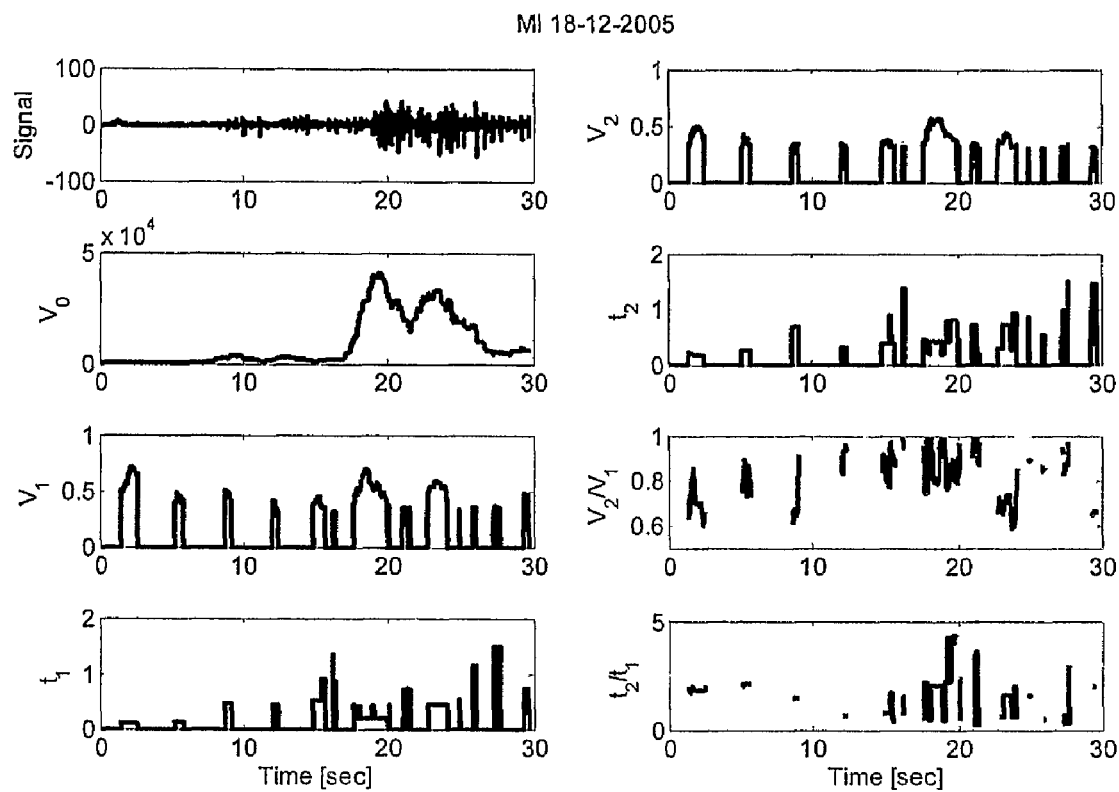
FIG. 12 illustrates epileptic seizure motion sensor readings.

Referring to FIG. 12, the motion signal parameters are illustrated of acceleration occurring in a single direction, as measured during a seizure. The values plotted (t1, v1, v0, etc.), were previously defined in relation to FIG. 10 hereinabove. The signal amplitude of the central peak (v0) is high only during the seizure (the second graph) (for example, above 1000). When the autocorrelation is weak, the first and second peaks are hardly detected, and their parameters are set to zero. t1 and t2 during epileptic seizures have characteristic values, below 2 and 4 seconds, respectively. As one can see, the values of these peaks—v1 and v2—are high at the seizure, such as above 0.3. The second peak is weaker than the first one, but strong enough, thus their ratio can be in the range [0.5, 1].

Figure 13:
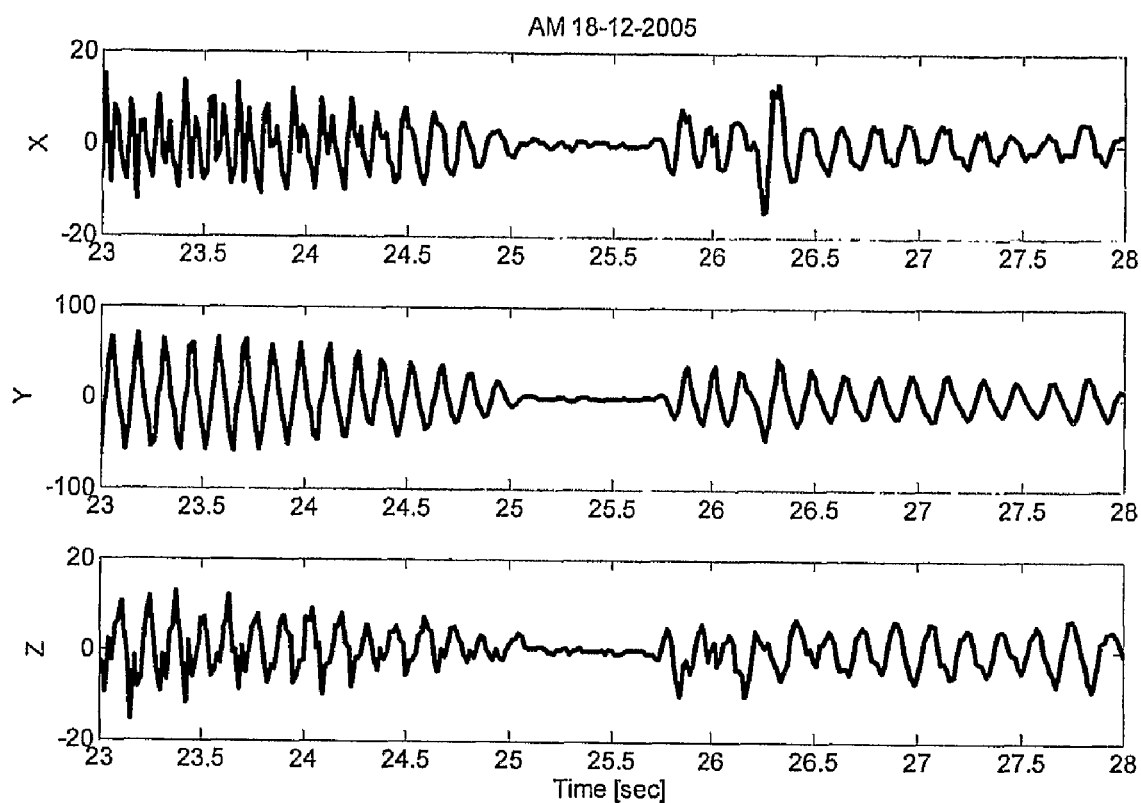
FIGS. 13 and 14 additionally illustrate epileptic seizure motion sensor readings for a severe seizure.

Referring to FIG. 13, similar parameters can be seen in another recorded signal, of another, much quicker and stronger epileptic seizure. In this seizure, the movement was mostly in the Y direction, as can be seen from its much higher acceleration values. Several behavioral changes occurred during this seizure, as one can see in the zooming in axial graphs. The acceleration was very quick at first, while later the acceleration became weaker and the repeatability—slower, with a nearly quiet period at the center of the enlarged portion.

Figure 14:
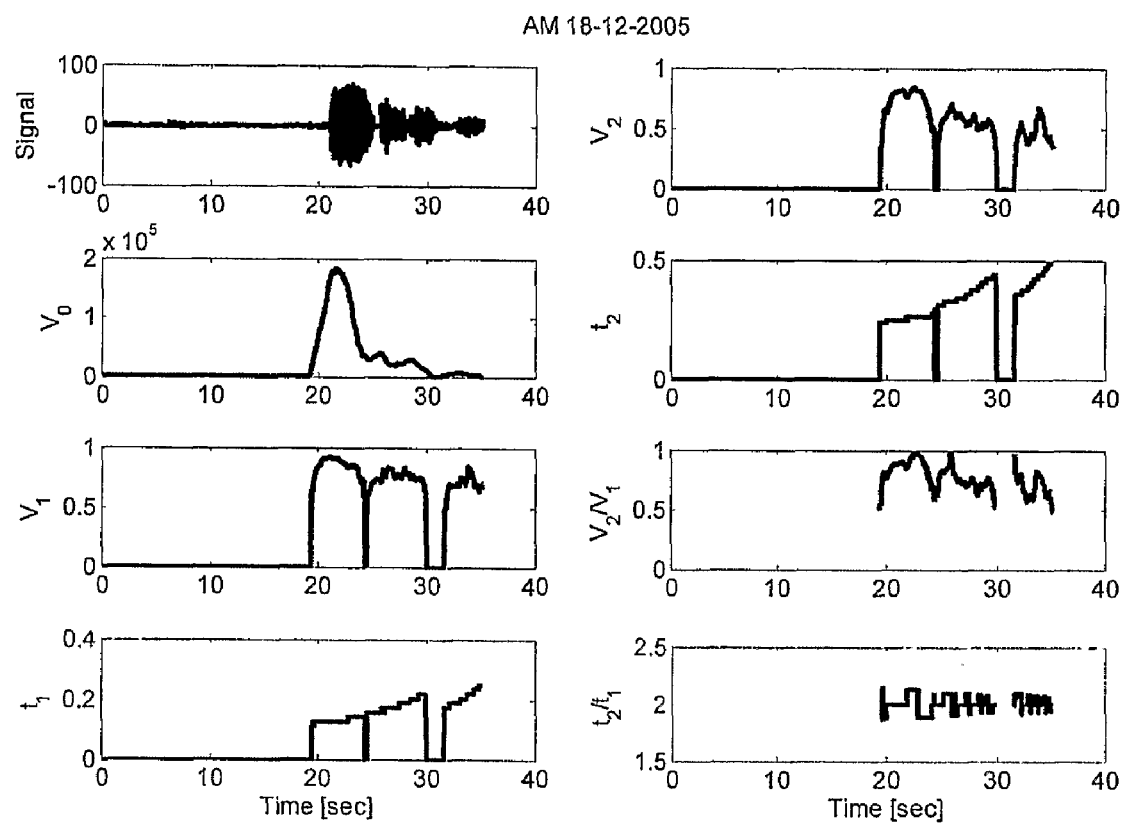

Referring to FIG. 14, the parameters are illustrated of acceleration occurring in a single direction, as measured during a seizure. A similar gap can also be seen in the parameters graphs, which begin prior to the seizure onset. The parameters also demonstrate that this is a much quicker and stronger epileptic motion.

Figure 15:
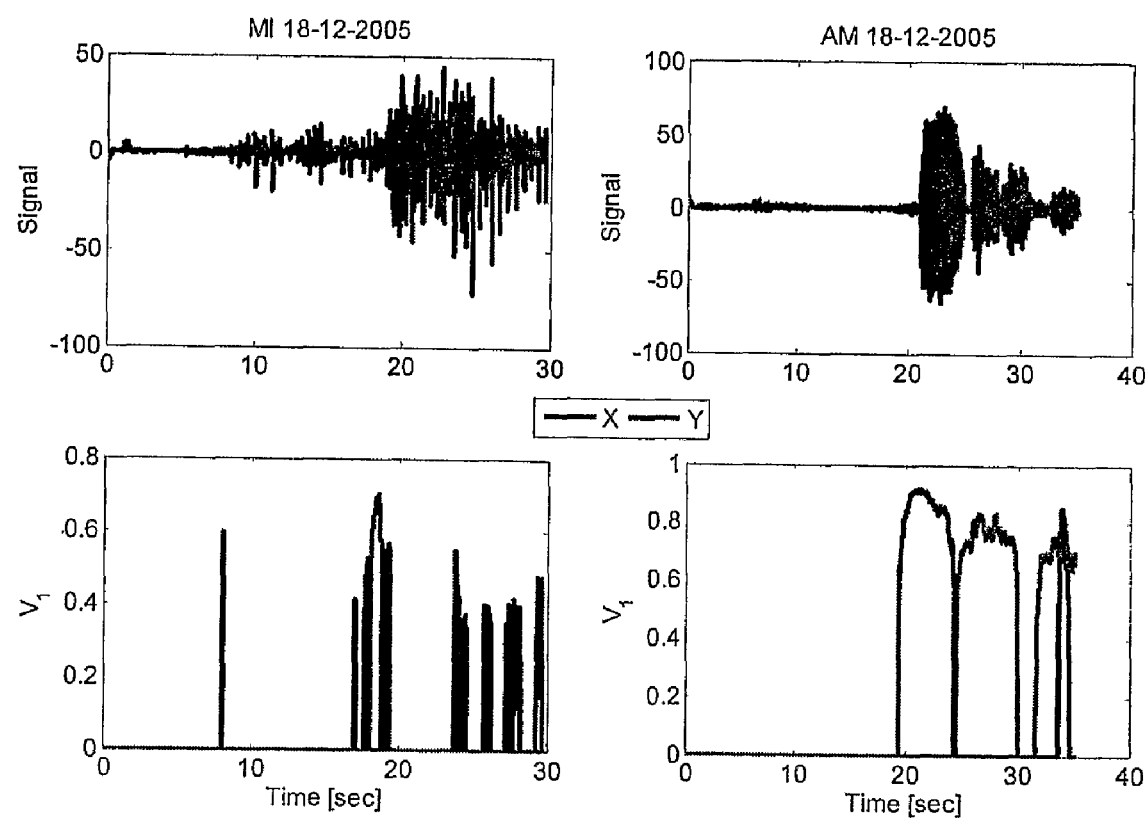
FIG. 15 illustrates epileptic seizure motion sensor readings, showing dominant axis changes during the seizure.

Referring to FIG. 15, motion signal parameters are depicted for two cases. The graphs at left (under the Ml heading) refer to one patient's seizures, while the graphs at right (under the AM heading) refer to another patient's seizures. Another parameter that can be used for seizure detection is the dominant axis changes during the seizure. Unlike a common movement, which generally has a defined direction over certain time period, the epileptic movement generally changes its spatial orientation frequently. Adding another highly active channel to the graphs above of the two epileptic seizures demonstrates this, when in the left size—MI recording, the X and Y axis are alternately the dominant movement axis (as seen in the axial graphs above). Similarly, in the AM recording, Y is the dominant axis, and in a short portion of the seizure, the X acceleration is also very strong. The same can happen for all the axes, including the Z axis.

Figure 16:
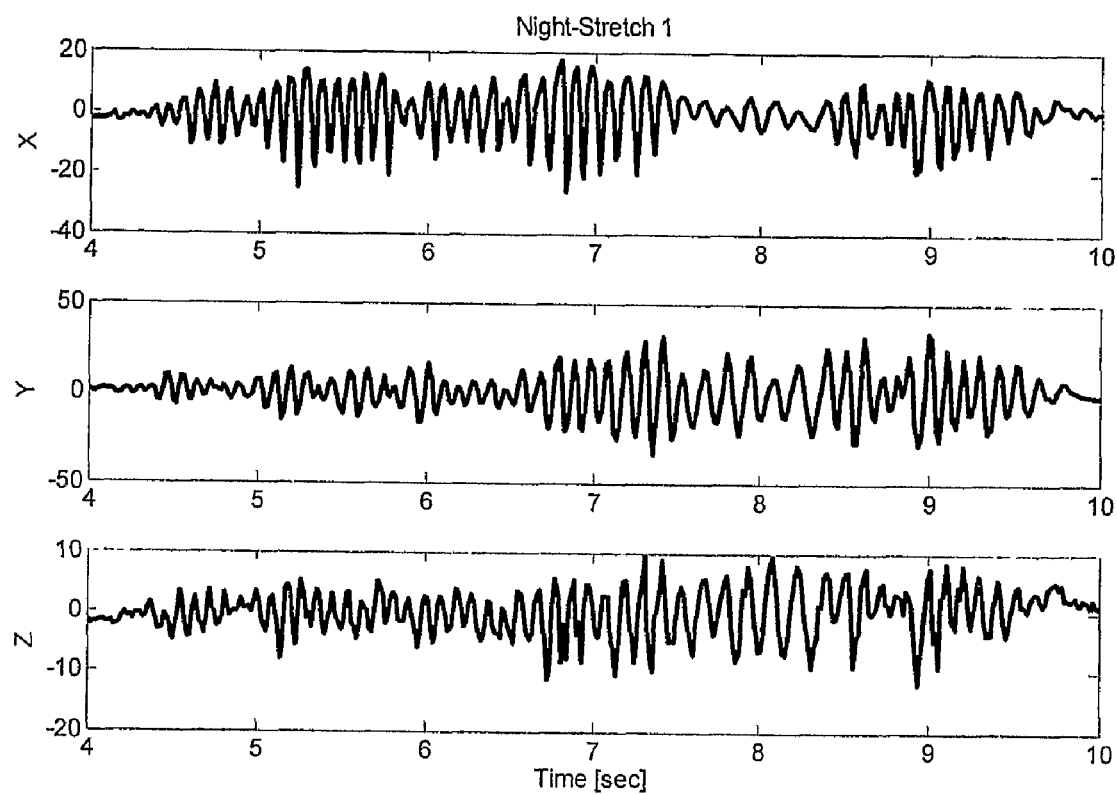
FIG. 16 illustrates a non-epileptic recording of a night stretch signal.

Referring to FIG. 16, the acceleration signals are depicted for a normal, non-epileptic motion, occurring during sleep, and termed a "night stretch" (stretching of the limbs occurring during normal sleep). The movement is similar to that occurring during epileptic event:

the physiological aspect—muscle tonus
the mathematical point of view—the right frequency and amplitude ranges.

Figure 17:
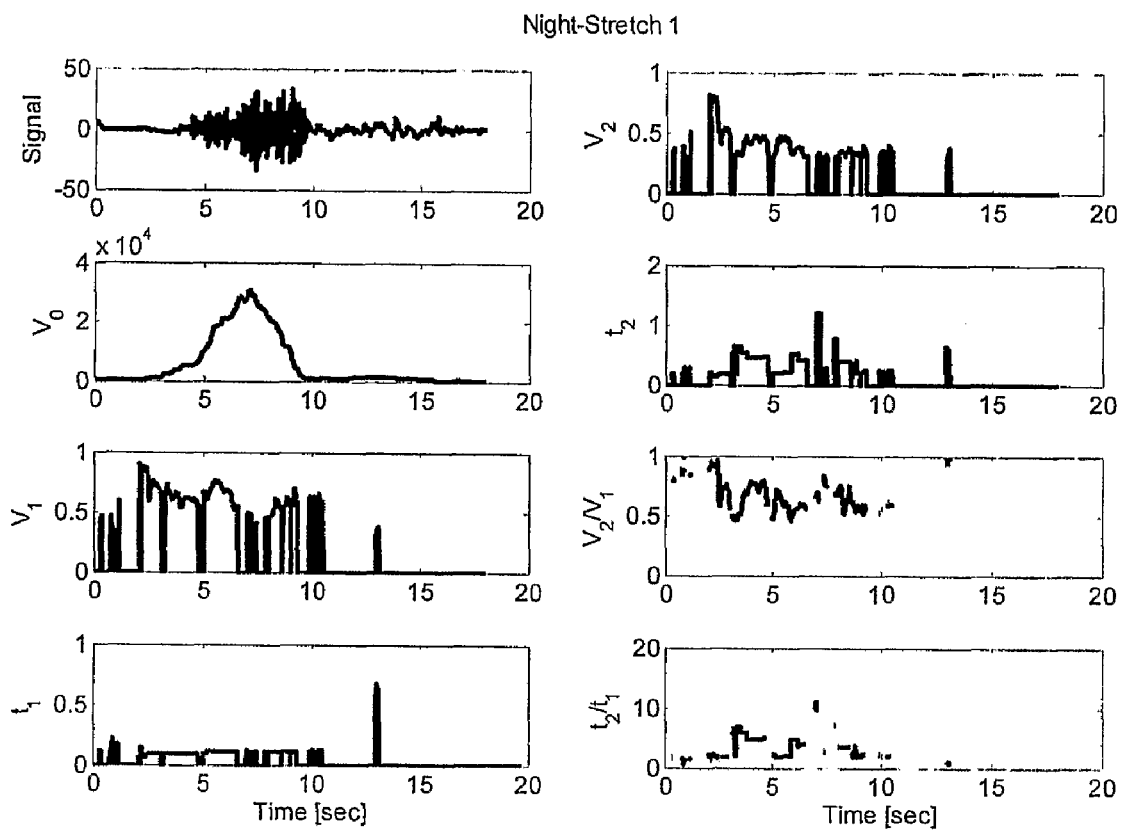
FIG. 17 illustrates parameters and analysis of FIG. 16.

Referring to FIG. 17, the signal parameters of the night-stretch are depicted, showing a tonic-like movement at a relatively low amplitude. The signal can be defined as non-epileptic due to its shortened duration.

Figure 18:
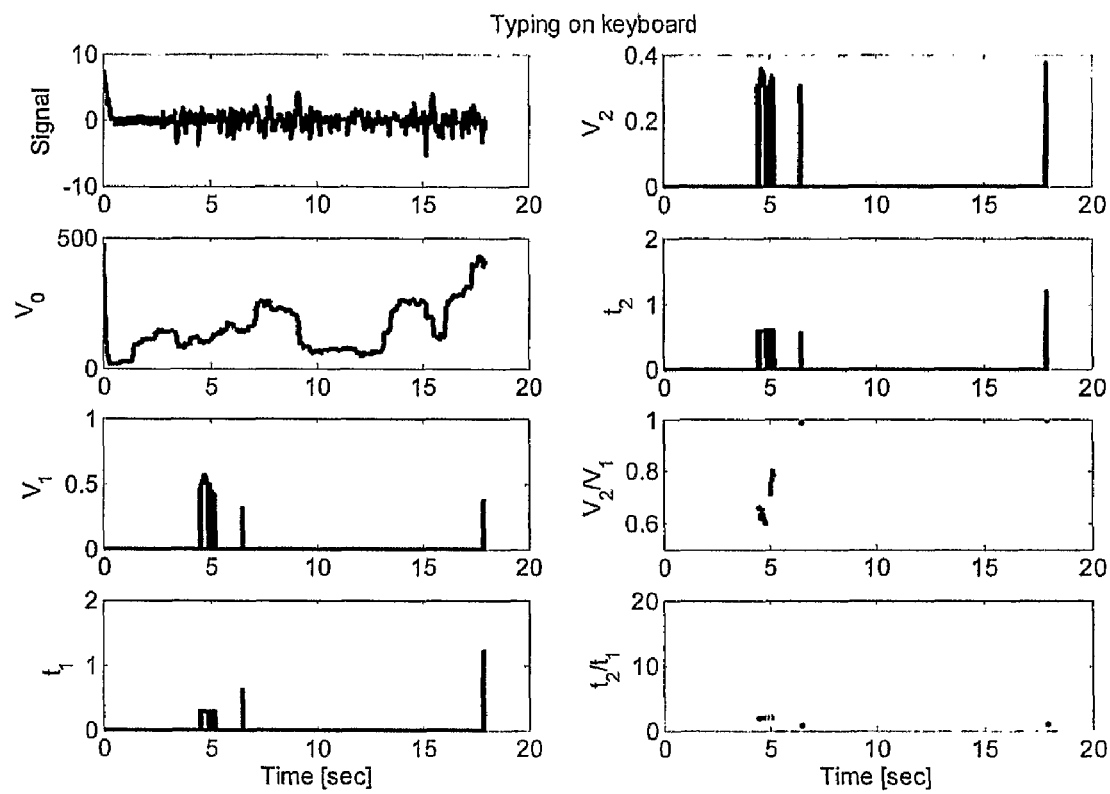
FIG. 18 illustrates a non-epileptic recording of typing on a keyboard.

Referring to FIG. 18, another daily movement is typing on the keyboard. The signal is shown in the graph at top left, while the signal motion parameters are shown in the remaining graphs. The signal associated with this normal movement is very weak, with low repeatability, and thus can be easily distinguished from an epileptic signal occurring during an epileptic event. This is the situation with most common movements.

Figure 19:
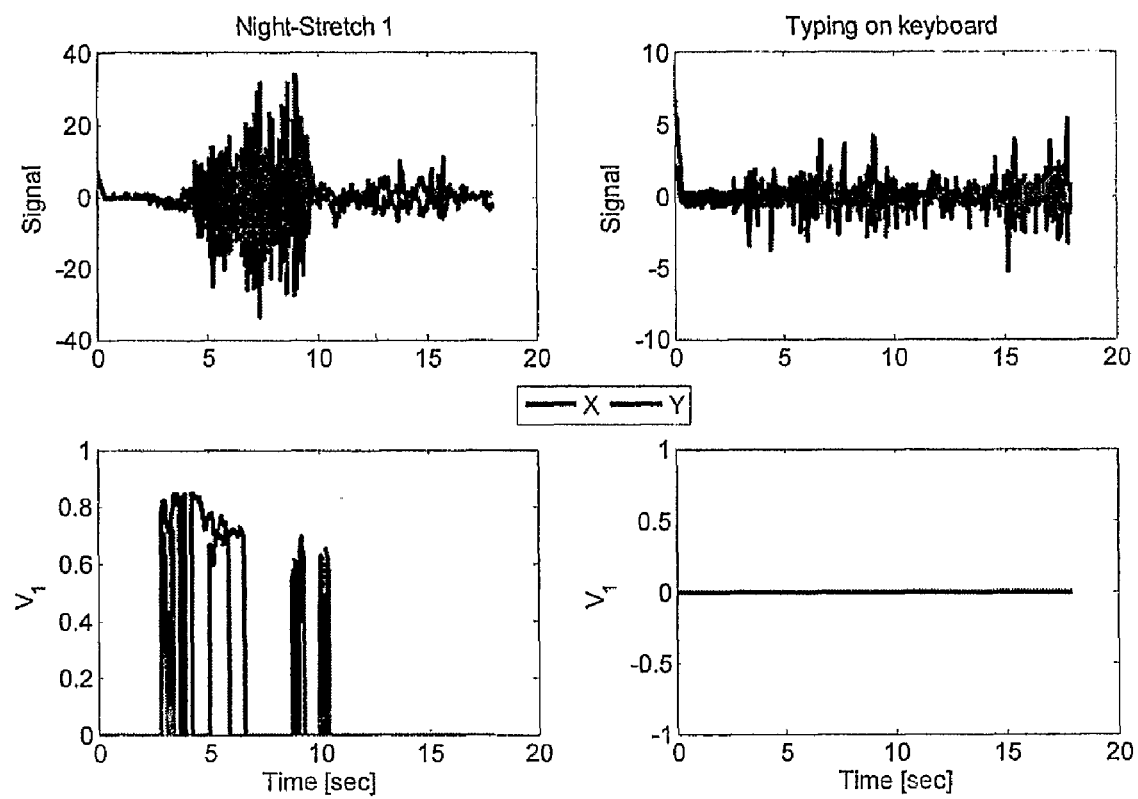
FIG. 19 illustrates parameters and analysis of FIGS. 16, 18.

Referring to FIG. 19, these daily movements also exhibit a much clearer axial direction, as can be seen when adding another axial signal.

In the night-stretch, the movement is in the XY axes, without short jolts in other directions, like the one seen in the epileptic recordings.

The typing signal is much too random and weak, thus no clear v1 can be detected, not to mention defining a directional behavior.

Embodiments of the present invention may include apparatuses for performing the operations herein. This apparatus may be specially constructed for the desired purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

The system of the invention may be used to detect additional pathologies related to motion events; there is no intention to limit the scope of the invention for use with epilepsy alone, rather additional pathological motion-related events may be detected by the system. A set of motion signal parameters of normal non-pathological motion may be stored in the non-volatile memory, as well as motion signal parameters associated with pathological motion. These may be used and compared to signal parameters for an individual as measured by the motion sensors of the invention. Thus, additional motion-related pathologies may be detected.

While certain features of the invention have been illustrated and described herein, many modifications, substitutions, changes, and equivalents will now occur to those skilled in the art. It is, therefore, to be understood that the appended claims are intended to cover all such modifications and changes as fall within the true spirit of the invention.

The invention claimed is:

1. A detection and analysis unit of an epileptic event alert system, the detection and analysis unit comprising:
   a) one or more motion sensors adapted to produce an electrical signal corresponding with mechanical movement of the detection and analysis unit;
   b) a microcontroller comprising:
      i. non-volatile memory adapted to store at least one set of motion signal parameters associated with epileptic motion and at least another set of parameters associated with non-epileptic motion;
      ii. computer readable software and dedicated hardware adapted to compare at least one signal parameter of the signal produced by said one or more sensors against at least one of said stored sets of motion signal parameters;
   c) a communication unit adapted to transmit an alert signal to a remote location.

2. The system according to claim 1, wherein each motion sensor produces a separate signal, and wherein the separate signal produced by each given sensor includes information relating to motion of said sensor in a direction corresponding with an orientation of the given sensor.

3. The system according to claim 2, wherein any one or more of the separate signals reaching the threshold level causes a power management circuit in said control circuit to induce a power-saving mode in said system when the signals have not reached the threshold level for a predefined duration time.

4. The system according to claim 2, wherein the signal produced by said one or more motion sensors is an analog signal and system further comprises an analog to digital converter.

5. The system according to claim 1, wherein said software (ii) is adapted to output a seizure probability value based on a comparison of parameters of the signal produced by said one or more sensors and the stored set of motion signal parameters associated with epileptic motion.

6. The system according to claim 5, wherein the seizure probability value is additionally based on a comparison of parameters of the signal produced by said one or more sensors and the stored set of motion signal parameters associated with non-epileptic motion, and wherein the seizure probability value is positively related to a correlation between the sensor signal parameter with one or more parameters in the parameter set associated with epileptic movement and inversely related to a correlation between the sensor signal parameter with one or more parameters in the parameter set associate with non-epileptic movement.

7. The system according to claim 5, further comprising an alert decision unit adapted to produce a local alert signal based on the seizure probability value and based on a predefined duration of signal.

8. The system according to claim 7, wherein the local alert signal produced by said decision unit is adapted to trigger said communication unit to transmit a remote alert signal.

9. The system according to claim 7, further comprising a switch operable by the user, for deactivating a local alert signal prior to a remote alert signal being triggered.

10. The system according to claim 1, wherein said communication unit utilizes wireless communication to transmit said alert signal to a remote location.

11. The system according to claim 1, further comprising an output signal for instructing an epileptic treatment unit to administer an epileptic treatment in response to an alert signal.

12. The system according to claim 11, wherein said epileptic treatment unit applies a treatment substantially automatically in response to either a local or remote alert signal.

13. The system according to claim 11, wherein said epileptic treatment unit is adapted to be triggered by a treatment signal initiated remotely and received through said communication unit.

14. The system according to claim 1, further comprising a visual display activated by said control circuit; and wherein the microcontroller is adapted to initiate a self-test.

15. The system according to claim 1, further comprising a microphone for detecting sounds originating in the vicinity of the user, and said communication unit is adapted to transmit said sounds detected by said microphone.

16. the system according to claim 1, wherein said control circuit is adapted to trigger an alert when no motion signals are detected during a predefined period of time.

17. The system according to claim 1, wherein said signal parameters produced by said motion sensor and said stored epileptic motion signal parameters, are selected from at least one of the following group: the frequency of the motion, frequency variation over time, the amplitude of the signal, amplitude variations over time, the relative direction of the motion, the direction variation over time, and the duration of the motion.

18. The system according to claim 1, wherein said system is adapted to be worn upon the limb of a user.

19. The system according to claim 18, wherein said system has the general appearance of a wristwatch.

20. The system according to claim 1, further comprising a recorder, adapted to store and allow retrieval of at least one of the following: motion signal parameters of a user, processed motion signal parameters, and alert signal transmission data.

21. A method of detecting an epileptic seizure comprising:
   a. fastening at least one motion sensor to the limb of a user, said sensor adapted to produce electrical signals corresponding with mechanical movement of the sensor, the sensor being operative to output a separate electrical signal for movement in each of the X,Y,Z axes;
   b. measuring said electrical signals produced by said at least one motion sensor and performing computerized processing of said signals to obtain signal motion parameters, the signal motion parameters including frequency of motion;
   c. comparing said parameters of said measured electrical signals, against at least one stored set of epileptic motion signal parameters and/or against at least one set of non-epileptic epileptic motion signal parameters, wherein said comparison is performed using computerized processing means;
   d. outputting a seizure probability value based on said comparison;
   e. transmitting an alert signal to a remote location, using a communication unit, if said seizure probability value is within a predetermined range of values.

22. The method according to claim 21, wherein said signal parameters measured by said motion sensor and said stored motion signal parameters, are further comprised of at least one of the following: frequency variation over time, the amplitude of the signal, amplitude variations over time, the relative direction of the motion, the direction variation over time, and the duration of the motion.

23. The method according to claim 21, further comprising a step of autocorrelation, performed during said step (b), wherein said autocorrelation is performed upon the signal measured by each sensor, or performed upon signals measured by different sensors of said system.

24. The method according to claim 21, further comprising a step of removal of DC bias, performed during said step (b).

25. Computer-readable media storing a computer program that when executed performs steps (b), (c) and (d) of claim 21, wherein the computer-readable media is a disk, read-only memory (ROM), random access memory (RAM), electrically programmable read-only memory (EPROM), electrically erasable and programmable read only memory (EEPROM), magnetic card, or optical card.

26. The computer-readable media according to claim 25, the computer program being further adapted to initiate transmission of the alert signal to the remote location, using the communication unit, if said seizure probability value is within the predetermined range of values.

27. A detection and analysis unit of an alert system for detection and identification of pathological motion events, the detection and analysis unit comprising:
  a) one or more motion sensors adapted to produce an electrical signal corresponding with mechanical movement of the detection and analysis unit;
  b) a microcontroller comprising:
    i. non-volatile memory adapted to store at least one set of motion signal parameters associated with pathological motion and at least another set of parameters associated with normal non-pathological motion;
    ii. computer readable software and dedicated hardware adapted to compare at least one signal parameter of the signal produced by said one or more sensors against at least one of said stored sets of motion signal parameters;
  c) a communication unit adapted to transmit an alert signal to a remote location.

\* \* \* \* \*